United States Patent [19]
Cannata et al.

[11] Patent Number: 5,856,570
[45] Date of Patent: Jan. 5, 1999

[54] PROCESS FOR PREPARING 5-AMINO-2,4,6-TRIIODOISOPHTHALIC ACID DICHLORIDE BY CHLORINATION OF THE CORRESPONDING ACID IN THE PRESENCE OF A TERTIARY AMINE SALT OR QUATERNARY AMMONIUM SALT

[75] Inventors: Vincenzo Cannata, Sasso Marconi; Corrado Velgi, Sarego; Giuseppe Barreca, Milan, all of Italy

[73] Assignee: Bracco International B.V., Amsterdam, Netherlands

[21] Appl. No.: 836,984

[22] PCT Filed: Nov. 24, 1995

[86] PCT No.: PCT/EP95/04635

§ 371 Date: May 29, 1997

§ 102(e) Date: May 29, 1997

[87] PCT Pub. No.: WO96/16927

PCT Pub. Date: Jun. 6, 1996

[30] Foreign Application Priority Data

Nov. 29, 1994 [IT] Italy .................................. MI94A2412

[51] Int. Cl.$^6$ ..................................................... C07C 63/00
[52] U.S. Cl. ............................................................ 562/855
[58] Field of Search ............................................... 562/855

[56] References Cited

U.S. PATENT DOCUMENTS 5,616,795   4/1997   Mauro et al. .......................... 562/855

*Primary Examiner*—Paul J. Killos
*Attorney, Agent, or Firm*—Oblon, Spivak, McClelland, Maier & Neustadt, P.C.

[57] ABSTRACT

A process for the preparation of 5-amino-2,4,6-triiodoisophthalic acid dichloride by chlorinating 5-amino-2,4,6-triiodoisophthalic acid with thionyl chloride in the presence of a suitable solvent and of a tertiary amine salt or quaternary ammonium salt in a molar ratio from 1;1 to 1;2 with respect to 5-amino-2,4,6-triiodoisophathalic acid is described. 5-amino-2,4,6-triiodoisophthalic acid dichloride is an intermediate useful for the preparation of iodinated contrast agents.

14 Claims, No Drawings

PROCESS FOR PREPARING 5-AMINO-2,4,6-TRIIODOISOPHTHALIC ACID DICHLORIDE BY CHLORINATION OF THE CORRESPONDING ACID IN THE PRESENCE OF A TERTIARY AMINE SALT OR QUATERNARY AMMONIUM SALT

This application is a 371 of PCT/EP95/04635 filed 24 Nov. 1995.

The present invention relates to a process for the preparation of an intermediate useful in the synthesis of organic compounds and, more particularly, it relates to a process for the preparation of 5-amino-2,4,6-triiodoisophthalic acid dichloride.

5-Amino-2,4,6-triiodoisophthalic acid dichloride is a known compound useful for the preparation of iodinated contrast agents among which Iopamidol (British patent No. 1,472,050—Savac AG) and Ioversol (European patent application No. 0083964 Mallinckrodt Inc.) can be cited.

Several examples of synthesis of 5-amino-2,4,6-triiodoisophthalic acid dichloride are reported in the literature and all of them foresee the chlorination of 5-amino-2,4,6-triiodoisophthalic acid with thionyl chloride.

In particular, we can cite the syntheses described in the already mentioned British patent No. 15 1,472,050, in the Belgian patent No. 852,418 (Mallinckrodt Inc.) and in the U.S. Pat. No. 3,655,752 (Sterling Drug Inc.) which use a strong excess of thionyl chloride and which require a long and cumbersome work up, hardly suitable under an industrial viewpoint, even if in some cases they allow to afford the desired dichloride with high yields.

The synthesis described in the European patent application No. 0118347 (Guerbet S.A.) foresees the use of excess thionyl chloride too, but in the presence of catalytic amounts of N,N-dimethylformamide. The yields are high but the work up requires the removal of excess thionyl chloride by evaporation also in this case.

The use of solvents such as ethyl acetate, as described in the International patent applications No. WO 91/09007 (Mallinckrodt Inc.) and No. WO 93/10825 (Mallinckrodt Inc.) or in the already mentioned European patent application No. 0083964, does not allow to obtain the desired dichloride with satisfactory yields.

We have now found that, by carrying out the chlorination reaction of 5-amino-2,4,6-triiodoisophthalic acid with thionyl chloride in a suitable solvent in the presence of a tertiary amine salt or quaternary ammonium salt, the corresponding dichloride is obtained not only in high yields but also substantially free from impurities and in crystalline form by simple dilution of the reaction mixture with water.

Therefore, object of the present invention is a process for the preparation of 5-amino-2,4,6-triiodoisophthalic acid dichloride by chlorination of 5-amino-2,4,6-triiodoisophthalic acid with thionyl chloride in the presence of a solvent characterized in that the reaction is carried out in the presence of a tertiary amine salt or quaternary ammonium salt in a molar ratio from 1:1 to 1:2 with respect to 5-amino-2,4,6-triiodoisophthalic acid.

The 5-amino-2,4,6-triiodoisophthalic acid dichloride obtained according to the process of the present invention is useful as intermediate in the synthesis of Iodinated contrast agents.

The amount of thionyl chloride used in the process object of the present invention is generally from 2 to 8 moles with respect to 5-amino-2,4,6-triiodoisophthalic acid.

Preferably, from 4 to 6 moles of thionyl chloride by mole of 5-amino-2,4,6-triiodoisophthalic acid are used.

Tertiary amine salts which can be used in the process object of the present invention are generally hydrohalides, preferably hydrochlorides or hydrobromides.

Quaternary ammonium salts which can be used in the process object of the present invention are generally halides, preferably chlorides or bromides.

The tertiary amines are generally trialkylamines, preferably trethylamine.

Quaternary ammonium salts are generally tetraalkvlammonium salts, preferably tetraethylammonium or tetrabutylammoniuum salts.

Examples of tertiary amine salts and of quaternary ammonium salts used in the process object of the present invention are triethylamine hydrochloride, triethylamine hydrobromide, tetrabutylammonium chloride, tetrabutylammonium bromide, tetraethylammonium bromide and tetraethylammonium chloride.

Preferably triethylamine hydrochloride, which can be optionally prepared in situ, is used. The amount of tertiary amine salt or quaternary ammonium salt is preferably equimolar (molar ratio 1:1) with respect to 5-amino-2,4,6-triiodoisophthalic acid. Suitable solvents are ethyl acetate, methylene chloride, chloroform and 1,2-dichloroethane. Preferably methylene chloride is used.

A preferred practical embodiment of the present invention is the following. Thionyl chloride is added to a suspension of 5-amino-2,4,6-triiodoisophthalic acid, triethylamine and methylene chloride and the reaction mixture is heated under reflux for some hours.

At the end of the addition, water is added and the precipitation of a crystalline product is observed.

By simple filtration and washing, 5-amino-2,4,6-triiodoisophthalic acid dichloride is obtained in pure form.

The characterizing feature of the process object of the invention is the presence of amounts at least equimolar of a tertiary amine salt or of a quaternary amine salt.

The use of said salt in the above indicated amounts allows to obtain the desired product with extremely high yields and, above all, free from impurities which should make difficult its isolation with a purity degree suitable for its use as intermediate in the synthesis of iodinated contrast agents.

It is worth underlining that the substantial absence of by-products in the reaction of preparation of 5-amino-2,4,6-triiodoisophthalic acid dichloride according to the process object of the present invention does not result exclusively in an improvement of the overall yield of the process with respect to the known methods, but allows also the isolation of the desired product with simple operations of dilution in water of the reaction mixture.

It is evident to the man skilled in the art the advantage deriving from the possibility of carrying out a process for the synthesis of an intermediate with high yields, high purity, through extremely simple operations, without requiring either the removal of thionyl chloride by evaporation or repeated purification operations for isolating the desired product in pure form.

As already underlined, contrary to what described in the known processes for the preparation of 5-amino-2,4,6-triiodoisophthalic acid dichloride, the isolation of the pure product is carried out by simple dilution with water of the reaction mixture.

As far as we know, a mechanism able to explain the unexpected advantages deriving from the use of a tertiary amine salt or of a quaternary ammonium salt according to the process object of the present invention cannot be assumed.

Probably, the salt forms an adduct with thionyl chloride.

In this connection, it is worth noting that the literature (European patent application No. 0026281—Bracco Industria Chimica S.p.A.) describes the preparation of 5-methylamino2,4,6-triiodoisophthalic acid dichloride by reaction with thionyl chloride in the presence of small amounts of quinoline, without reporting the yields yet.

However, the use of quinoline or of a tertiary amine salt or quatemary ammoniun salt in molar amounts significantly lower than 1:1 with respect to 5-amino-2,4,6-triiodoisophthalic acid does not allow to obtain the desired product with high yields and, above all, with a suitable purity degree. In particular, by using quinoline in catalytic amounts as described in the European patent application No. 0026281, the desired dichloride is obtained in admixture with not negligible amounts of by-products and then with a purity degree not suitable for the use as intermediate in the subsequent steps of the process for the preparation of iodinated contrast agents.

In order to illustrate the present invention the following examples are now given.

EXAMPLE 1

Methylene chloride (280 g), triethylamine (25.5 g; 0.25 moles) and water (2.25 g; 0.125 moles) were charged in this order into a reactor.

After addition of thionyl chloride (14.9 g; 0.125 moles) dropwise while keeping the temperature below 30° C., 5-amino-2,4,6-triiodoisophthalic acid (140 g; 0.25 moles) and, in about 1.5 hours, thionyl chloride (143 g; 1.2 moles) were added while keeping the internal temperature below 36° C. and adjusting the addition rate with the gas emission.

At the end of the addition, the reaction mixture was kept under reflux (43° C.) for 28 hours. After cooling to about 30° C., methylene chloride (65 g) and, in small portions, water (100 g) were added.

At about half of the addition, the formation of a crystalline precipitate was observed.

After filtration, the resultant product was reduced to pulp with water (200 g) and then dried in oven under vacuum at 60° C. for about 21 hours obtaining 5-amino-2,4,6-triiodoisophthalic acid dichloride (139 g; 93.3% yield) practically pure by HPLC analysis and by thin layer chromatography.

EXAMPLE 2

Methylene chloride (280 g), triethylamine (51 g; 0.5 moles) and water (4.5 g; 0.25 moles) were charged in this order into a reactor.

After addition of thionyl chloride (30 g; 0.25 moles) dropwise while keeping the temperature below 30° C., 5-amino-2,4,6-triiodoisophthalic acid (140 g; 0.25 moles) and, in about 2 hours, thionyl chloride (143 g; 1.2 moles) were added while keeping the internal temperature below 36° C. and adjusting the addition rate with the gas emission.

At the end of the addition, the reaction mixture was kept under reflux (about 43° C.) for 22 hours.

After cooling to about 30° C., water (100 g) was added in small portions.

At about half of the addition, the formation of a crystalline precipitate was observed.

Subsequently, the addition of water (250 g total) was completed and the precipitate was filtered.

The resultant product was reduced to pulp twice with water (2×300 g) and then dried in oven under vacuum at 60° C. for about 21 hours obtaining 5-amino-2,4,6-triiodoisophthalic acid dichloride (140.7 g; 94.4% yield) practically pure by HPLC analysis and by thin layer chromatography.

EXAMPLE 3

Methylene chloride (112 g) and tetrabutylammonium bromide (3.23 g; 0.1 moles) were charged in this order into a reactor.

5-Amino-2,4,6-triiodoisophthalic acid (55.9 g; 0.1 moles) and, in about 2 hours, thionyl chloride (57.1 g; 0.479 moles) were added to the mixture while keeping the internal temperature below 36° C. and adjusting the addition rate with the gas emission.

At the end of the addition, the reaction mixture was kept under reflux (43° C.) for 27 hours.

After cooling to about 20° C., water (60 g) was added in small portions.

At about half of the addition, the formation of a crystalline precipitate was observed.

After filtration, the resultant product was washed with water (5×50 g) and then dried in oven under vacuum at 50° C. for about 21 hours obtaining 5-amino-2,4,6-triiodoisophthalic acid dichloride (49.99 g; 83.8% yield) practically pure by HPLC analysis and by thin layer chromatography.

We claim:

1. A process for the preparation of 5-amino-2,4,6-triiodoisophthalic acid dichloride by chlorination of 5-amino-2,4,6-triiodoisophthalic acid with thionyl chloride in the presence of a solvent characterized in that the reaction is carried out in the presence of a tertiary amine salt or quaternary ammonium salt in a molar ratio from 1:1 to 1:2 with respect to 5-amino-2,4,6-triiodoisophthalic acid.

2. A process according to claim 1 wherein the amount of thionyl chloride is from 2 to 8 moles by mole of 5-amino-2,4,6-triiodoisophthalic acid.

3. A process according to claim 2 wherein the amount of thionyl chloride is from 4 to 6 moles by mole of 5-amino-2,4,6-triiodoisophthalic acid.

4. A process according to claim 1 wherein the tertiary amine salts or quaternary amine salts are tertiary amine hydrohalides or quaternary ammonium halides.

5. A process according to claim 4 wherein the salts are tertiary amine hydrochlorides or hydrobromides or quaternary ammonium chlorides or bromides.

6. A process according to claim 1 wherein the tertiary amines are trialkylamines.

7. A process according to claim 6 wherein the tertiary amine is triethylamine.

8. A process according to claim 1 wherein the quaternary ammonium salts are tetraalkylammonium salts.

9. A process according to claim 8 wherein the quaternary ammonium salt is selected among tetraethylammonium and tetrabutylammonium salts.

10. A process according to claim 1 wherein the tertiary amine salts or quaternary ammonium salts are selected among triethylamine hydrochloride, triethylamine hydrobromide, tetrabutylammonium chloride, tetrabutylammonium bromide, tetraethylammonium bromide and tetraethylammonium chloride.

11. A process according to claim 10 wherein triethylamine hydrochloride is used.

12. A process according to claim 1 wherein the amount of tertiary amine salt or quaternary ammonium salt is equimolar with respect to 5-amino-2,4,6-triiodoisophthalic acid.

13. A process according to claim 1 wherein the solvent is selected among ethyl acetate, methylene chloride, chloroform and 1,2-dichloroethane.

14. A process according to claim 13 wherein the solvent is methylene chloride.

* * * * *